US009848849B2

(12) United States Patent
Pfeiffer et al.

(10) Patent No.: US 9,848,849 B2
(45) Date of Patent: Dec. 26, 2017

(54) SYSTEM AND METHOD FOR TOUCH SCREEN CONTROL OF AN ULTRASOUND SYSTEM

(75) Inventors: Jeffrey Scott Pfeiffer, Waukesha, WI (US); Brent Jason Lavin, Wauwatosa, WI (US); Kimberly A. Canova, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 240 days.

(21) Appl. No.: 12/196,170

(22) Filed: Aug. 21, 2008

(65) Prior Publication Data
US 2010/0049046 A1    Feb. 25, 2010

(51) Int. Cl.
    *A61B 8/00*       (2006.01)
    *A61B 8/13*       (2006.01)

(52) U.S. Cl.
    CPC .............. *A61B 8/13* (2013.01); *A61B 8/4405* (2013.01); *A61B 8/4472* (2013.01); *A61B 8/4477* (2013.01)

(58) Field of Classification Search
    CPC ..... A61B 8/13; A61B 8/4472; C11D 11/0047; C11D 7/26; B08B 3/04
    USPC ....................................................... 600/437
    See application file for complete search history.

(56) References Cited

U.S. PATENT DOCUMENTS

| | | | |
|---|---|---|---|
| 5,255,682 A * | 10/1993 | Pawluskiewicz et al. | .... 600/459 |
| 5,961,457 A * | 10/1999 | Raylman et al. | ............. 600/436 |
| 6,135,958 A | 10/2000 | Mikula-Curtis et al. | |
| 6,139,496 A * | 10/2000 | Chen et al. | .................... 600/437 |
| 6,468,212 B1 * | 10/2002 | Scott | ........................ A61B 8/00 600/437 |
| 6,497,661 B1 | 12/2002 | Brock-Fisher | |
| 6,575,908 B2 | 6/2003 | Barnes et al. | |
| 6,599,244 B1 | 7/2003 | Epps et al. | |
| 6,638,223 B2 | 10/2003 | Lifshitz et al. | |
| 6,980,419 B2 | 12/2005 | Smith et al. | |
| 7,022,075 B2 | 4/2006 | Grunwald et al. | |
| 2002/0044059 A1 * | 4/2002 | Reeder et al. | ............. 340/573.1 |
| 2003/0013966 A1 | 1/2003 | Barnes et al. | |
| 2003/0078501 A1 | 4/2003 | Barnes et al. | |
| 2003/0195418 A1 | 10/2003 | Barnes et al. | |

(Continued)

FOREIGN PATENT DOCUMENTS

WO    WO 2006106335 A1 * 10/2006 ............. A61B 5/103

OTHER PUBLICATIONS

Oxford Dictionaries, http://www.oxforddictionaries.com/definition/english/module, Jul. 7, 2012.*

(Continued)

*Primary Examiner* — Christopher Cook
(74) *Attorney, Agent, or Firm* — Dean D. Small; The Small Patent Law Group, LLC

(57) ABSTRACT

An ultrasound system includes a display device and a processor module. The display device is configured to display an ultrasound image. At least a portion of the display device includes a touch sensitive portion that is responsive to a touch in each of a plurality of user selectable elements presented on the display device. The processor module is configured to adjust at least one of the ultrasound image and an imaging setting based on the touch in at least one of the user selectable elements of the display device. The ultrasound image and the user selectable elements are concurrently displayed on the display device.

32 Claims, 9 Drawing Sheets

(56) References Cited

U.S. PATENT DOCUMENTS

| | | | |
|---|---|---|---|
| 2004/0138569 A1* | 7/2004 | Grunwald et al. | 600/459 |
| 2005/0079896 A1* | 4/2005 | Kokko | G06F 3/0488 455/566 |
| 2005/0124890 A1* | 6/2005 | Halmann et al. | 600/446 |
| 2006/0082518 A1* | 4/2006 | Ram | 345/1.1 |
| 2007/0182663 A1* | 8/2007 | Biech | G06F 1/1618 345/1.1 |
| 2008/0062625 A1* | 3/2008 | Batio | G06F 1/1615 361/679.29 |
| 2008/0119731 A1* | 5/2008 | Becerra et al. | 600/437 |
| 2008/0146922 A1* | 6/2008 | Steins | A61B 8/546 600/437 |
| 2008/0194951 A1* | 8/2008 | Poland | A61B 8/00 600/437 |
| 2008/0306382 A1* | 12/2008 | Guracar et al. | 600/437 |
| 2009/0131793 A1 | 5/2009 | Stonefield et al. | |
| 2009/0198132 A1* | 8/2009 | Pelissier | A61B 8/00 600/443 |

OTHER PUBLICATIONS

Computer Hope, http://www.computerhope.com/issues/ch000791.htm, Mar. 23, 2006, pp. 1-6.*

Ultrasound designed for vascular access, www.sonosite.com, ©2004 SonoSite, Inc., 2 pgs.

ILook° Personal Imaging Tool—User Guide, www.sonosite.com, ©2004 SonoSite, Inc., 102 pgs.

SonoSite iLook/Overview, Nov. 25, 2008, 2 pgs.

VascuView, The Most Advanced Visual Ultrasound Device for Assisted Vascular Access, http://www.escalonmed.com/eva/vvprod..html, Nov. 25, 2008, 2 pgs.

Portable Performance LOGIQ 3, © 2005 General Electric Company, www.gehealthcare.com, 6 pgs.

GE Healthcare-Product Features—LOGIQ, GE Healthcare, © 2009 General Electric Company, 2 pgs.

GE Healthcare-Product Features—LOGIQ 7, Ultrasound, GE Healthcare, © 2009 General Electric Company, 2 pgs.

GE Healthcare-Product Features—LOGIQ 9, Ultrasound, GE Healthcare, © 2009 General Electric Company, 2 pgs.

SonixTOUCH The New Face of Ultrasound, Ultrasonix Medical Corporation, www.ultrasonix.com/touch, 00.050.040 Rev. A, 8 pgs.

A.Unique, Patented Convertible Ultrasound™ Platform, Zonare; www.zonare.com/technology, 2005 3 pgs.

B-K Medical announces world's first operating room ultrasound docking system, B-K Medical, Herley, Denamark, Nov. 20, 2001, 2 pgs.

* cited by examiner

SYSTEM AND METHOD FOR TOUCH SCREEN CONTROL OF AN ULTRASOUND SYSTEM

BACKGROUND OF THE INVENTION

This invention relates generally to medical imaging systems, and more particularly to ultrasound imaging systems.

Known ultrasound imaging systems include a display device and a user interface used in conjunction with one another to obtain an ultrasound image from ultrasound beams emitted by a transducer probe. The display device presents the ultrasound image while the user interface permits an operator to control the functions, operations, image settings, adjustments to the ultrasound image, and the like. For example, the user interface in known systems includes a keyboard. The operator types keystrokes using the keyboard to change the display of the ultrasound image and/or adjust one or more settings of the ultrasound system. These systems frequently are used in environments where the keyboard is exposed to fluids. For example, these systems may be used in emergency rooms and other surgical suites. The fluids can enter into the keyboard and damage the keyboard. Moreover, the keyboard in such systems typically is formed of porous materials, which make sterilization of the keyboards more difficult than non-porous components of the system.

Some known ultrasound systems include an additional display device that includes a touch sensitive portion. One display device displays the ultrasound image while the additional display device displays one or more touch sensitive buttons. The operator cannot concurrently view the ultrasound image and the touch sensitive buttons on the same display device. Moreover, the controls and functions that may be changed by the operator touching the touch sensitive buttons on the display device are limited in known systems. Additional functions and controls must be adjusted using the keyboard of the system. Thus, access to the keyboard is still necessary to permit complete control of the ultrasound system.

A need therefore exists to provide an operator with an ultrasound imaging system that allows greater control over the settings, functions and controls of the ultrasound system, while protecting the user interface of the system. A need also exists to permit the operator to concurrently view the ultrasound image with displayed controls that reduces or eliminates the use of other controls.

BRIEF DESCRIPTION OF THE INVENTION

In one embodiment, an ultrasound system includes a display device and a processor module. The display device is configured to display an ultrasound image. At least a portion of the display device includes a touch sensitive portion that is responsive to a touch in each of a plurality of user selectable elements presented on the display device. The processor module is configured to adjust at least one of the ultrasound image and an imaging setting based on the touch in at least one of the user selectable elements of the display device. The ultrasound image and the user selectable elements are concurrently displayed on the display device.

In another embodiment, a method for presenting an ultrasound image includes displaying the ultrasound image on a display device and concurrently displaying a plurality of user selectable elements on the display device in at least one touch sensitive portion of the display device, where the user selectable elements correspond to a plurality of image adjustments. The method also includes receiving a selection of at least one of the image adjustments by touching a corresponding one of the user selectable elements and adjusting the ultrasound image according to the selected image adjustment.

In another embodiment, a computer-readable storage medium for adjusting a display of an ultrasound image includes instructions for concurrently displaying the ultrasound image and a plurality of user selectable elements on a display device, where the user selectable elements are displayed in at least one touch sensitive portion of the display device and representative of a plurality of image adjustments; instructions for sensing a touch of at least one of the user selectable elements to select a corresponding one of the image adjustments; and instructions for applying the image adjustment selected by the touch of at least one of the user selectable elements to adjust the ultrasound image.

DETAILED DESCRIPTION OF THE INVENTION

Figure 1:
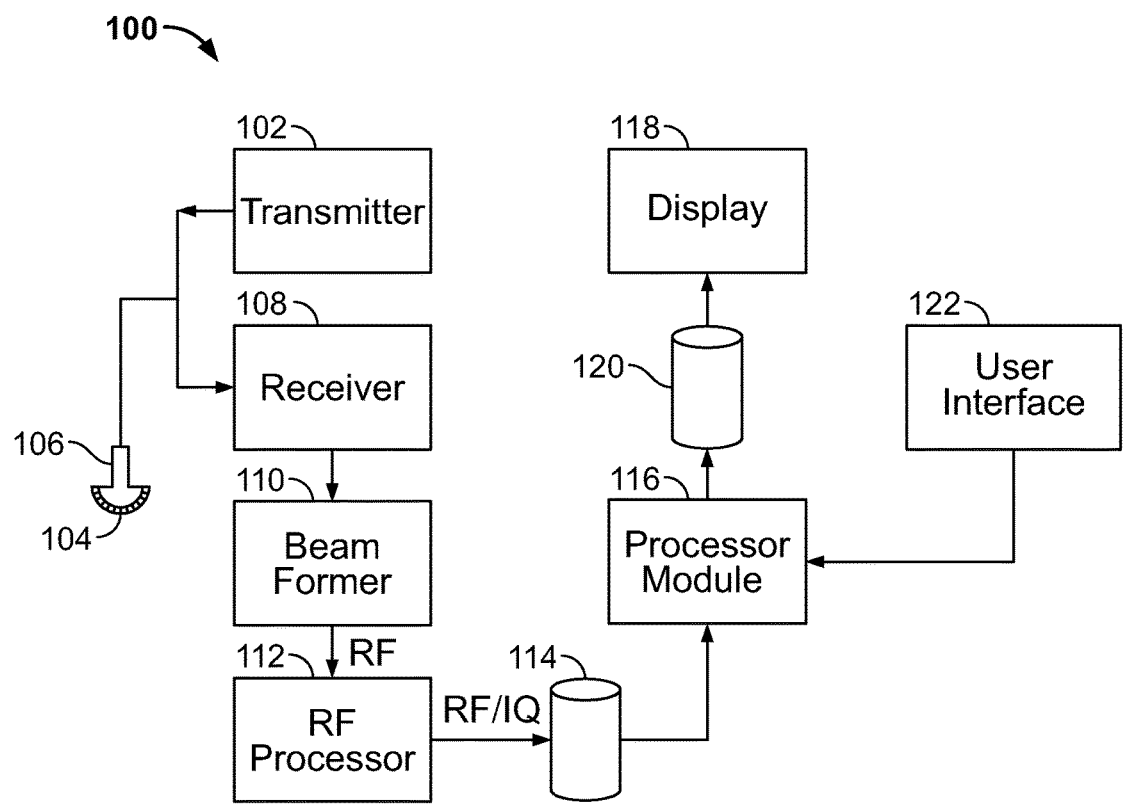
FIG. 1 illustrates a block diagram of an ultrasound system according to one embodiment.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor or random access memory, hard disk, or the like). Similarly, the programs may be stand alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although one or more embodiments may be described in connection with an ultrasound system, the embodiments described herein are not limited to ultrasound systems. In particular, one or more embodiments may be implemented in connection with different types of image display systems, including, by way of example only, other medical diagnostic imaging systems.

Example embodiments of systems and methods for calculating and displaying information are described in detail below. In particular, a detailed description of one or more embodiments of systems and methods for controlling an ultrasound system using a touch screen interface is provided. At least one technical effect of one or more embodiments described herein includes concurrently displaying an ultrasound image alongside a plurality of touch sensitive user selectable elements on a single display device, where the user selectable elements may be touched to adjust the ultrasound image and/or control the ultrasound system.

FIG. 1 illustrates a block diagram of an ultrasound system 100 according to one embodiment. The ultrasound system 100 includes a transmitter 102 that drives an array of elements 104, for example, piezoelectric crystals, within a transducer 106 to emit pulsed ultrasonic signals into a body or volume (not shown). A variety of geometries may be used and the transducer 106 may be provided as part of, for example, different types of ultrasound probes. The ultrasonic signals are back-scattered from structures in the body, for example, blood cells or muscular tissue, to produce echoes that return to the elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a computer-readable memory 114 for storage (for example, temporary storage).

The ultrasound system 100 also includes a processor module 116 to process the acquired ultrasound information (for example, RF signal data or IQ data pairs) and prepare frames of ultrasound information for display on a display device 118. The processor module 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 114 during a scanning session and processed in less than real-time in a live or off-line operation. A computer-readable image memory 120 is included for storing processed frames of acquired ultrasound information that are not scheduled to be displayed immediately. The image memory 120 may comprise any known data storage medium, for example, a permanent storage medium, removable storage medium, and the like.

The processor module 116 is connected to a user interface 122 that may control some operations of the processor module 116 as explained below and is configured to receive inputs from an operator or user of the system 100. The display device 118 includes one or more monitors that present patient information, including diagnostic ultrasound images to the user for review, diagnosis and analysis. At least a portion of the display device 118 includes a touch sensitive portion, as described below. The display device 118 may control some operations of the processor module 116 also as explained below. The display device 118 may automatically display, for example, planes from two-dimensional (2D) and/or three-dimensional (3D) ultrasound data sets stored in the memory 114 and/or 120. One or both of the memory 114 and the memory 120 may store 3D data-sets of the ultrasound data, where such 3D data sets are accessed to present 2D and 3D images. The processing of the data, including the data sets, is based in part on user inputs, for example, user selections received at the user interface 122.

In one embodiment, the connections among the components of the system 100 include one or more wired and/or wireless connections. For example, the display device 118 may be wirelessly connected to the processor module 116. A wireless connection can permit the display device 118 to be remotely located from the processor module 116 and the user interface 122. For example, the display device 118 may be located in an emergency room or surgery suite while one or more remaining components of the system 100 are located in another room, suite or building.

In operation, the system 100 acquires data, for example, volumetric data sets by various techniques (for example, 3D scanning, real-time 3D imaging, volume scanning, 2D scanning with transducers having positioning sensors, freehand scanning using a voxel correlation technique, scanning using 2D or matrix array transducers, and the like). Ultrasound images are displayed to an operator or user of the system 100 on the display device 118. The operator may then manipulate, alter or adjust the ultrasound images using one or more image adjustments. By way of example only, the image adjustments include one or more of a change in the depth of the field of view in the ultrasound image, the gain of the ultrasound image, the frequency of the ultrasound waves emitted by the elements 104 to obtain the ultrasound image, the focal position of the ultrasound waves emitted by the elements 104, and the imaging mode used to obtain the ultrasound image. For example, the imaging mode may be switched between two or more of B-mode, color, pulsed wave ("PW"), power Doppler Imaging ("PDI"), and M-mode imaging. The particular image adjustments that are selected by the operator may be selected by the operator touching one or more graphically displayed areas or buttons presented on a touch sensitive portion of the display device 118. Alternatively, the image adjustments may be selected by using one or more keystrokes on a keyboard that is part of, or operatively connected to, the user interface 122. In one embodiment, the system 100 only permits one of the display device 118 and the user interface 122 to control which image adjustments are performed on the displayed ultrasound image.

Figure 2:
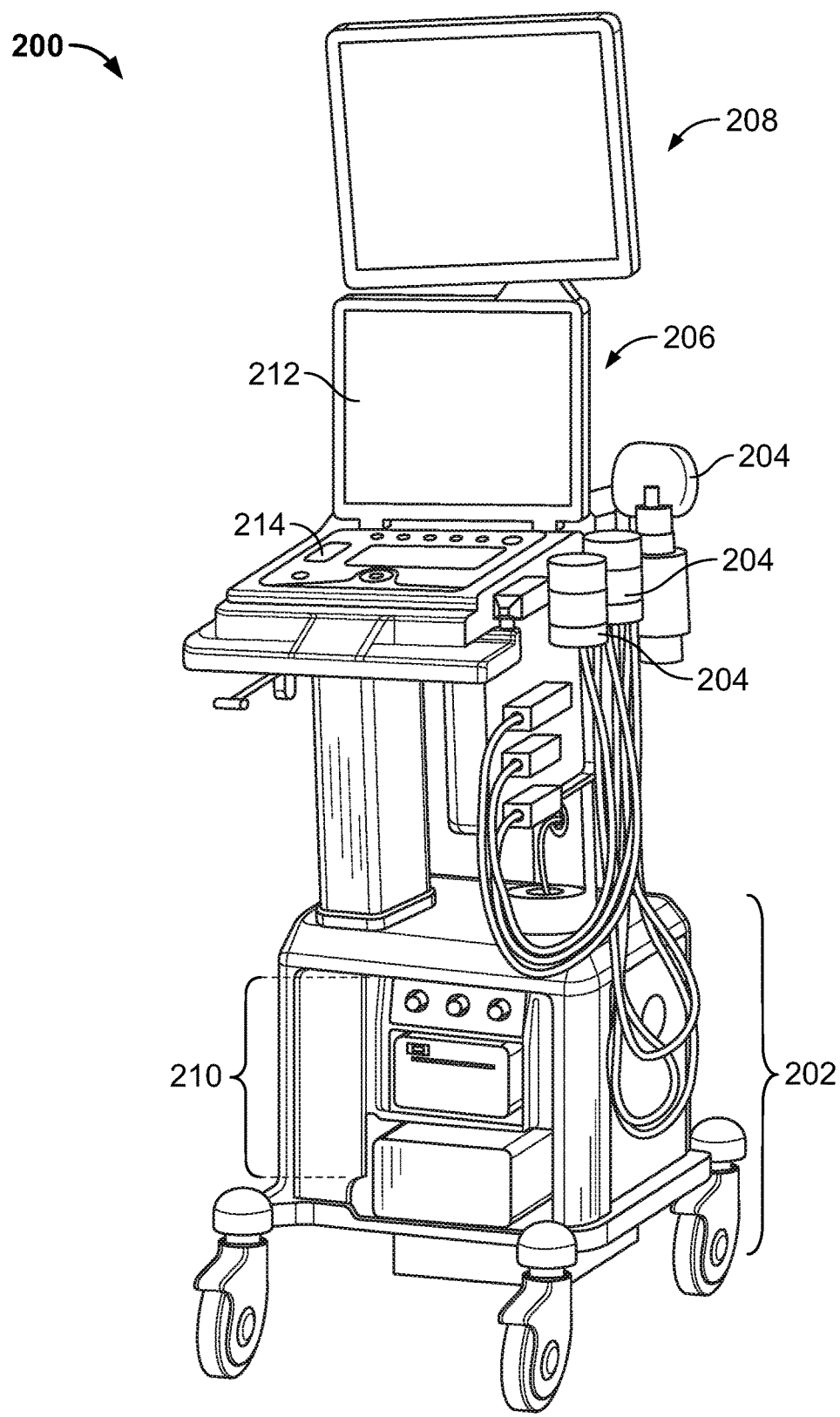
FIG. 2 is a perspective view of a console-based ultrasound imaging system provided on a movable base in accordance with one embodiment.

FIG. 2 is a perspective view of a console-based ultrasound imaging system 200 provided on a movable base 202 in accordance with one embodiment. The system 200 may be similar to the system 100 (shown in FIG. 1). For example, the system 200 includes one or more transducers 204 that are similar to the transducer 106 (shown in FIG. 1), a user interface 206 that is similar to the user interface 122 (shown in FIG. 1) and a display device 208 that is similar to the display device 118 (shown in FIG. 1) in one embodiment. The system 200 includes a controller 210 that includes one or more of a transmitter (not shown) that is similar to the transmitter 102. (shown in FIG. 1), a receiver (not shown) that is similar to the receiver 108 (shown in FIG. 1), a beam former (not shown) that is similar to the beam former 110 (shown in FIG. 1), an RF processor (not shown) that is similar to the RF processor 112 (shown in FIG. 1), one or more computer-readable storage media (not shown) that are similar to one or more of the memories 114, 120 (shown in FIG. 1), and a processor module (not shown) that is similar to the processor module 116 (shown in FIG. 1). The controller 210 may be embodied in one or more computers, microprocessors, servers, and the like. The user interface 206 may include a laptop computer having docking functionality with the movable base 202.

In the illustrated embodiment, the user interface 206 includes a secondary display device 212 and an input device 214. The secondary display device 212 may be similar to the display device 118 (shown in FIG. 1). In one embodiment, the secondary display device 212 does not include any touch sensitive portions. For example, no part of the secondary display device 212 includes a touch screen in one embodiment. As shown in FIG. 2, the input device 214 may include a keyboard. Alternatively, the input device 214 may include one or more additional or different input devices such as a mouse, microphone, and the like. The secondary display device 212 and the input device 214 are similar to the displays and input devices of known ultrasound imaging systems in one embodiment. The ultrasound data obtained by the transducer 204 and the ultrasound images formed by the controller 210 may be displayed on the secondary display device 212. One or more adjustments to the ultrasound images displayed on the secondary display device 212 may be made using the input device 214. For example, an operator may use a keystroke to change the operating frequency or imaging mode of the ultrasound image displayed on the secondary display device 212.

The display device 208 is a touch sensitive display that displays ultrasound images in one embodiment. Alternatively, one or more portions of the display device 208 are touch sensitive portions. For example, at least a portion of the display device 208 is able to detect the location of an operator's touch on the display device 208. Various types of touch technologies are available for use in touch sensitive displays, including but not limited to touch sensitive elements such as capacitive sensors, membrane switches, and infrared detectors.

In one embodiment, at least one of the user interface 206 and the display device 208 are employed by an operator of the system 200 to control the system 200. For example, the display device 208 may be used to adjust one or more settings of the ultrasound image displayed on the display device 208. For example, the touch sensitive portion(s) of the display device 208 may be utilized to adjust the ultrasound image. Alternatively, the input device 214 may be used to adjust the ultrasound image. In one embodiment, while both the display device 208 and the user interface 206 are communicatively coupled with the controller 210, only one of the display device 208 and the user interface 206 is able to control the system 200 and/or adjust the ultrasound image at a time. For example, a keystroke may be entered using the input device 214 to switch control of the system 200 and/or control of image adjustments between the display device 208 and the user interface 206, and vice-versa. Alternatively, the secondary display device 212 may be coupled to the input device 214 using a hinge such that the secondary display device 212 may pivot downward toward the input device 214 to substantially close the user interface 206. The controller 210 switches control of the system 200 and/or of image adjustments from the user interface 206 to the display device 208 when the secondary display 212 is folded downward in one embodiment.

The controller 210 may switch control of the system 200 and/or of image adjustments back to the user interface 206 when the secondary display 212 is folded back away from the input device 214. Permitting the display device 208 to control one or more operations of the system 200 while the secondary display 212 is folded down on the input device 214 can protect the input device 214 from damage while allowing an operator full control of the system 200. For example, in one embodiment substantially all of the controls and operations capable of being carried out using the input device 214 are replicated with the display device 208. Thus, the operator can have the same controls and operations with respect to the system 200 regardless of whether the display device 208 or the user interface 206 is utilized to control the system 200. Alternatively, a subset of the controls and operations made possible through use of the input device 214 may be replicated through the display device 208. For example, the functions associated with printing an ultrasound image and adding an annotation and/or measurement to the ultrasound image are only carried out using the input device 214 and are not possible to carry out using the display device 208 in one embodiment. In another embodiment, both of the display device 208 and the user interface 206 may be employed to switch control of the system 200 and/or control of image adjustments.

Figure 3A:
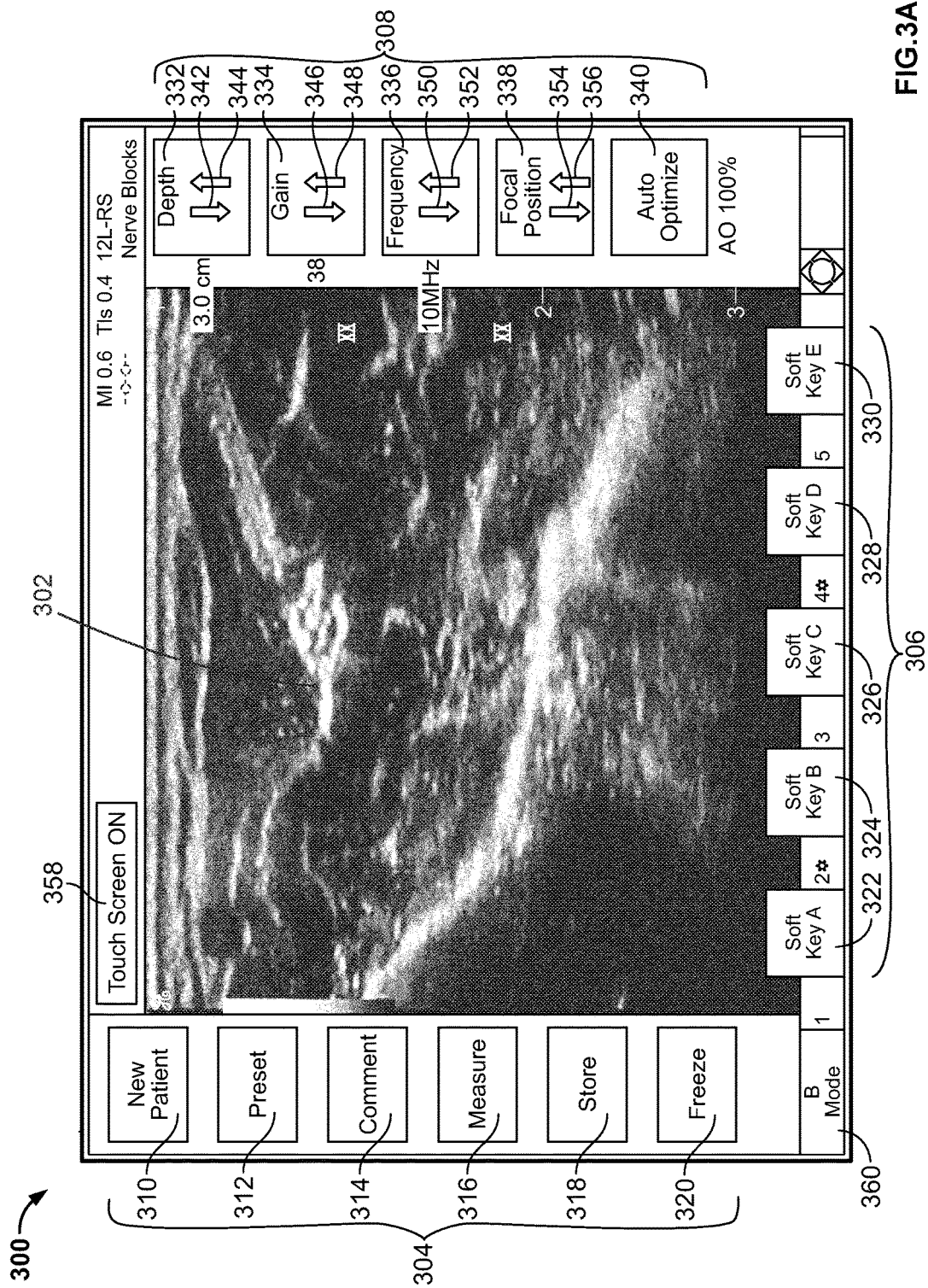
FIGS. 3A-B are illustrations of a view on display devices shown in FIG. 2.
Figure 3B:
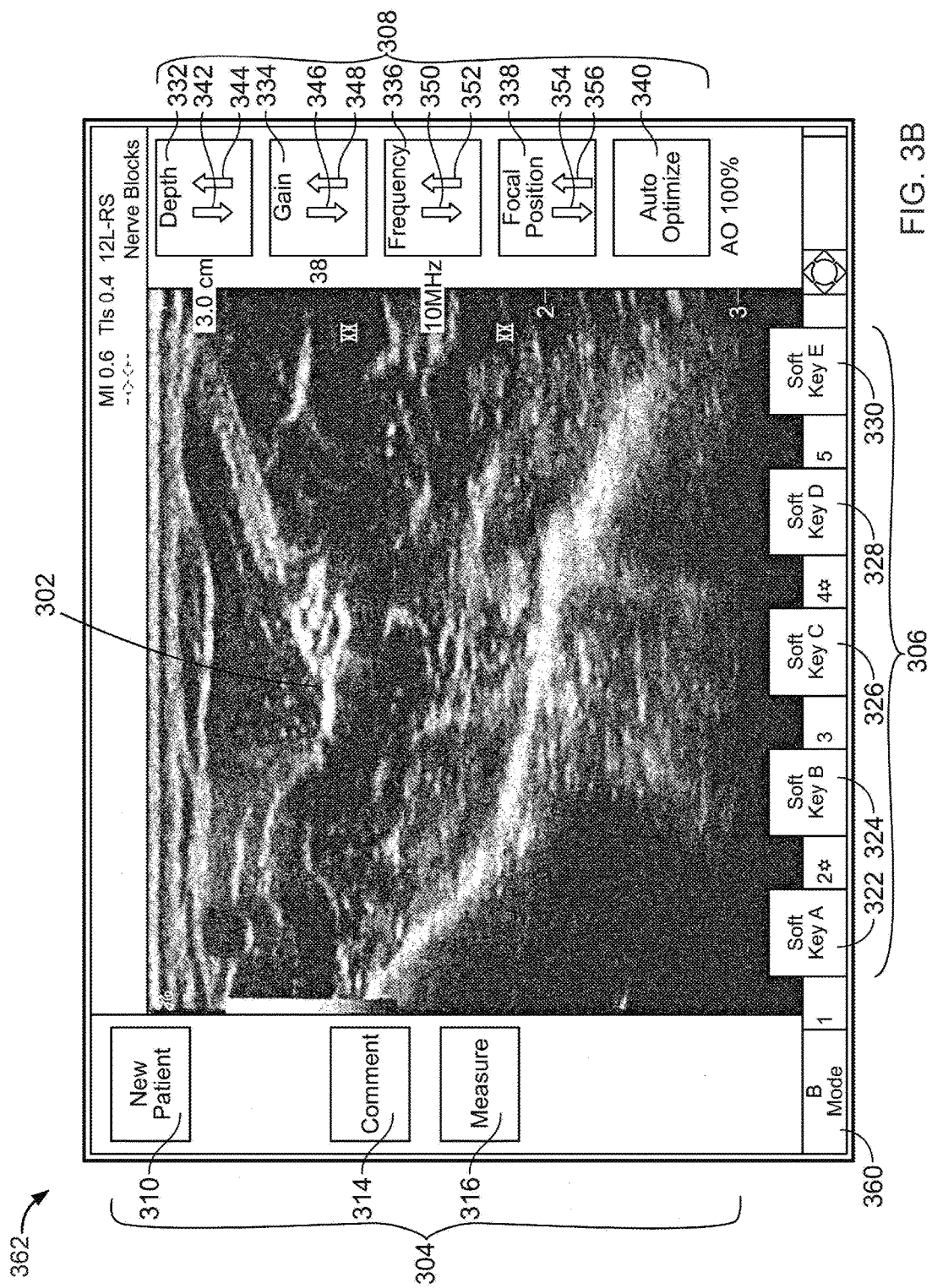

FIG. 3A is an illustration of a screenshot 300 of the display device 208 (shown in FIG. 2) according to one embodiment that provides touch screen functionality. FIG. 3B is an illustration of a screenshot 362 of the display device 212 (shown in FIG. 2) according to one embodiment. The screenshot 300 may be presented on substantially all or a subpart of the viewable portion of the display device 208. The screenshot 300 includes an ultrasound image 302 that is at least partially surrounded by a plurality of touch sensitive portions 304, 306, 308 of the display device 208 that are selectable by a user. Alternatively, substantially all of the display device 208 may include a touch sensitive portion. Moreover, while one particular layout of the screenshot 300 is shown in FIG. 3, other layouts, positions and orientations of the various components of the screenshot 300 are possible.

Each of the touch sensitive portions 304, 306, 308 includes a plurality of user selectable elements. For example, the touch sensitive portion 304 includes the user selectable elements 310 through 320, the touch sensitive portion 306 includes the user selectable elements 322 through 330, and the touch sensitive portion 308 includes the user selectable elements 332 through 340. One or more of the user selectable elements 310 through 340 represents a button or other interface capable of being touched by a user to control some aspect or feature of the system 200 (shown in FIG. 2) and/or to adjust the ultrasound image 302.

The controls, operations, functions, and the like (collectively referred to as "image adjustments") that are described below in conjunction with the various user selectable elements 310 through 340 are provided merely as examples and should not be construed as global limitations on one or more embodiments described herein. Touching the user selectable element 310 (in one embodiment, the "New Patient" area 310) can cause the system 200 to display patient information on the display device 208. For example, in one embodiment, touching the "New Patient" area 310 causes the display device 208 to graphically present the name, diagnosis, annotations, and the like, associated with the patient being imaged using the system 200.

Touching the user selectable element 312 (in one embodiment, the "Preset" area 312) causes the system 200 to load and/or apply a set of imaging parameters to the ultrasound image 302. For example, an operator of the system 200 may have a preferred group of imaging settings such as a preferred imaging frequency, imaging depth, focal point, and the like. These imaging settings may be stored in one or more of the memories 114, 120 (shown in FIG. 1) or the controller 210. Touching the "Preset" area 312 causes the system 200 to apply the imaging settings to the ultrasound image 302. Alternatively, touching the "Preset" area 312 can cause the display device 208 to present the operator with a list of groups of imaging settings (not shown). The operator may then touch a part of the display device 208 that corresponds to one of the groups of imaging settings to apply the corresponding imaging settings to the ultrasound image 302. In another embodiment, touching the "Preset" area 312 causes the display device 208 to present a list of available transducers 204 (shown in FIG. 2). The operator may touch a corresponding transducer 204 presented on the display device 208 to activate that transducer 204.

Figure 4:
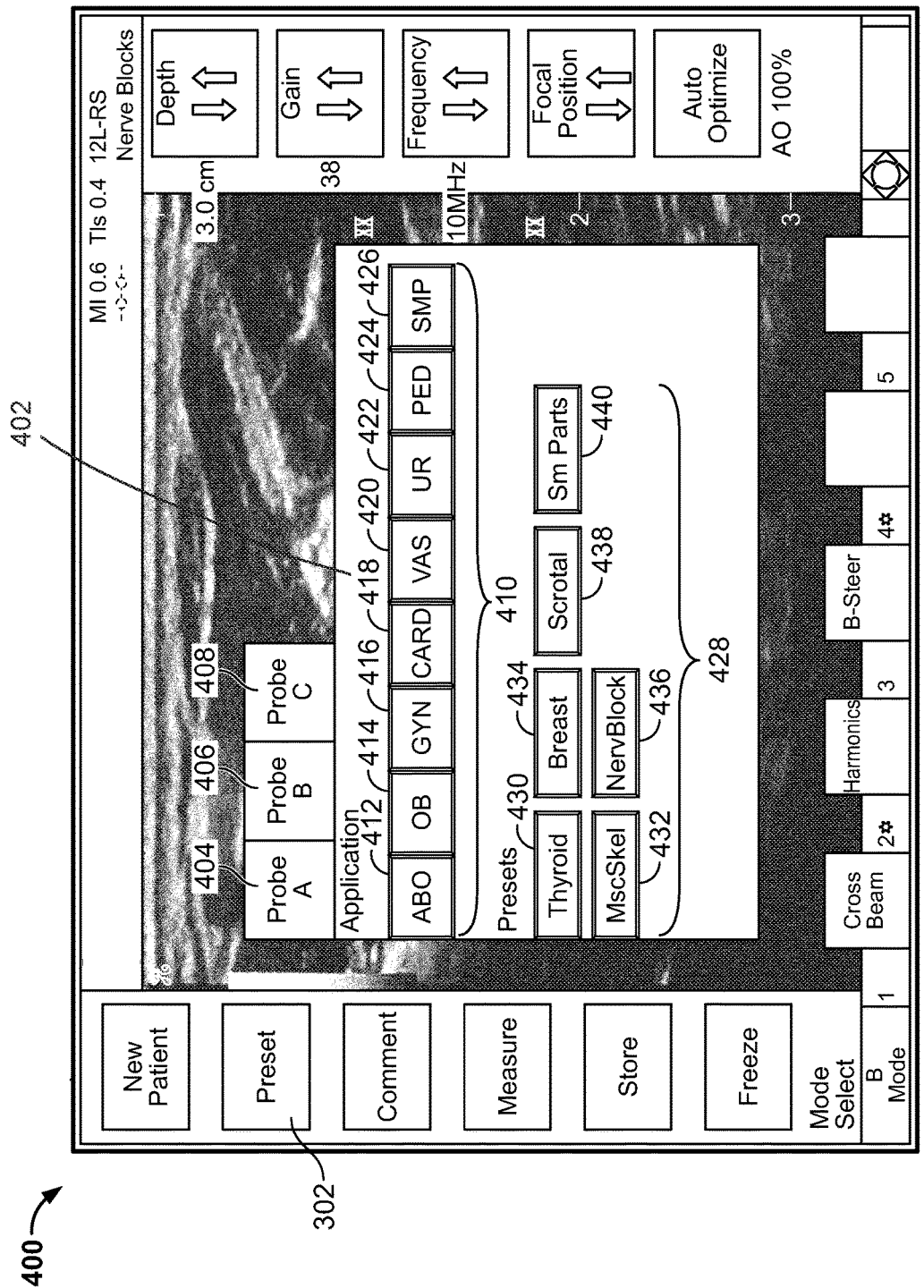
FIG. 4 is an illustration of another view on the display device shown in FIG. 2.

Upon selecting the "Preset" area 312 another view 400 is displayed on the display device 208 (shown in FIG. 2) according to one embodiment as shown in FIG. 4. In the illustrated embodiment, when the "Preset" area 312 is touched on the display device 208, a window 402 is populated on the display device 208. The window 402 includes a plurality of probe selection areas 404 through 408. Each of the probe selection areas 404 through 408 is associated with activation of a different transducer 204 (shown in FIG. 2). For example, touching the probe selection area 404 may activate a first transducer in the plurality of transducers 204 in the system 200 and deactivate one or more other transducers. The graphically defined window 402 includes a set 410 of application selection areas 412 through 426. Each of the application selection areas 412 through 426 is associated with automatically setting one or more imaging parameters of the system 200 according to a corresponding imaging application. For example, touching the area 418 may cause the system 200 to set one or more imaging parameters to obtain an ultrasound image 302 of a cardiovascular associated body, such as a heart. The imaging parameters may include the imaging mode, the frequency, the gain, and the like, of the ultrasound image 302. The graphically defined window 402 includes a set 428 of imaged body type selection areas 430 through 440. Each of the imaged body type selection areas 430 through 440 is associated with a different body part that is to be imaged by the system 200. For example, touching the selection area 434 may cause the system 200 to automatically set one or more imaging parameters to obtain an ultrasound image 302 of a breast, while touching the selection area 430 may cause the system 200 to automatically set one or more imaging parameters to obtain an ultrasound image 302 of a thyroid.

Returning to FIG. 3, touching the user selectable element 314 (in one embodiment, the "Comment" area 314) enables the operator of the system 200 to annotate the ultrasound image 302. For example, touching the "Comment" area 314 may cause the display device 208 to present a window or other field (not shown) in the screenshot 300. The operator may then input notes on the ultrasound image 302 in the window or other field. For example, the operator may use the input device 214 to type in a note concerning the ultrasound image 302. In one embodiment, a virtual keyboard or other input device is displayed on the display device 208 and is selectable by the operator to type in a note concerning the ultrasound image 302.

Touching the user selectable element 316 (in one embodiment, the "Measure" area 316) enables the operator of the system 200 to measure a feature in the ultrasound image 302. For example, touching the "Measure" area 316 may cause the system 200 to prompt the operator to identify two or more points on the ultrasound image 302 between or among which a measurement is to be made. The operator may then touch the display device 208 on the points between which the operator wishes to measure.

Touching the user selectable element 318 (in one embodiment, the "Store" area 318) causes the system 200 to save the ultrasound image 302 on a computer-readable storage medium in the controller 210 in one embodiment. For example, touching the "Store" area 318 may cause the system 200 to save the ultrasound image 302 along with one or more, or none, of annotations, measurements, and the like related to the ultrasound image 302. The ultrasound image 302 may be saved on a computer-readable storage medium such as the memories 114, 120 (shown in FIG. 1).

Touching the user selectable element 320 (in one embodiment, the "Freeze" area 320) causes the system 200 to freeze the ultrasound image 302 and display the ultrasound image 302 as a static image. For example, the ultrasound image 302 may be obtained and displayed in substantially real time. In order to pause the ultrasound image 302 so that the ultrasound image 302 does not move with respect to movement of the patient being examined and/or the transducer 204 (shown in FIG. 2), the operator can touch the "Freeze" area 320.

Touching the user selectable element 332 (in one embodiment, the "Depth adjustment" area 332) causes the system 200 to adjust the depth of the imaging field for the ultrasound image 302. The "Depth adjustment" area 332 may be subdivided into a decrease portion 342 and an increase portion 344. Touching the increase portion 344 causes the system 200 to increase the depth of the imaging field for the ultrasound image 302, while touching the decrease portion 346 causes the system 200 to decrease the depth of the imaging field.

Touching the user selectable element 334 (in one embodiment, the "Gain adjustment" area 334) causes the system 200 to adjust the gain of the ultrasound image 302. The "Gain adjustment" area 334 may be subdivided into a decrease portion 346 and an increase portion 348. Touching the increase portion 348 causes the system 200 to increase the gain of the ultrasound image 302, while touching the decrease portion 346 causes the system 200 to decrease the gain of the ultrasound image 302.

Touching the user selectable element 336 (in one embodiment, the "Frequency adjustment" area 336) causes the system 200 to adjust the frequency of the ultrasound image 302. The "Frequency adjustment" area 336 may be subdivided into a decrease portion 350 and an increase portion 352. Touching the increase portion 352 causes the system 200 to increase the frequency of the ultrasound beams emitted by the transducer 204 (shown in FIG. 2) used to obtain the ultrasound image 302, while touching the decrease portion 350 causes the system 200 to decrease the frequency of the ultrasound beams.

Touching the user selectable element 338 (in one embodiment, the "Focal position adjustment" area 338) causes the system 200 to adjust the focal point of the ultrasound beams in the object being imaged to obtain the ultrasound image 302. The "Focal position adjustment" area 338 may be subdivided into a decrease portion 354 and an increase portion 356. Touching the increase portion 356 causes the system 200 to increase the depth of the focal point of the ultrasound beams in the imaged object, while touching the decrease portion 354 causes the system 200 to decrease the depth of the focal point of the ultrasound beams in the imaged object.

Touching the user selectable element 340 (in one embodiment, the "Auto optimize" area 340) causes the system 200 to automatically adjust one or more imaging parameters. For example, based on a predetermined algorithm or logic, the controller 210 may automatically adjust imaging parameters such as the contrast of the ultrasound image 302 when the "Auto optimize" area 340 is touched.

In the illustrated embodiment, a value for each of the imaging parameters that are adjusted by touching the user selectable elements 332 through 340 is presented in a location that is proximate to the corresponding user selectable element 332 through 340. For example, as shown in FIG. 3, a current value of the imaging depth of 3.0 centimeters is presented by the display device 208 adjacent to the user selectable element 332, or the "Depth adjustment" area 332. Touching the "Depth adjustment" area 332 to adjust the imaging depth also causes the current value displayed on the display device 208 to change in a corresponding manner. For example, if the "Depth adjustment" area 332 is touched to increase the imaging depth, then the displayed value of the imaging depth also increases.

A graphic control indicator 358 is presented on the display device 208 in one embodiment. The graphic indicator 358 indicates whether the display device 208 or the user interface 206 has control of the system 200. For example, if the graphic indicator 358 indicates that the display device 208 has control of the system 200, then the touch sensitive portions 304, 306, 308 may be used to control operations of the system 200 while the user interface 206 may not be used to control the system 200 in one embodiment. Alternatively, if the graphic indicator 358 indicates that the user interface 206 has control of the system 200, then the touch sensitive portions 304, 306, 308 may not be used to control operations of the system 200 in one embodiment. In another embodiment, the graphic control indicator 358 is not presented on the display device 208.

A graphic mode indicator 360 is presented on the display device 208 in one embodiment. The graphic mode indicator 360 indicates what imaging mode is being used by the system 200 to obtain the ultrasound image 302. For example, the graphic mode indicator 360 may indicate that the system 200 is obtaining the ultrasound image 302 in any of B-mode, color, PW, PDI, M-mode imaging modes, and the like. In one embodiment, the graphic mode indicator 360 may be displayed on a touch sensitive portion such as on any of the touch sensitive portions 304, 306, 308. The graphic mode indicator 360 may then be touched to switch the imaging mode in which the system 200 is obtaining the ultrasound image 302. For example, the controller 210 may toggle among the plurality of imaging modes each time the graphic mode indicator 360 is touched. Alternatively, the system 200 may populate a list of possible imaging modes on the display device 208 once the graphic mode indicator 360 is touched. The operator of the system 200 may then touch the corresponding portion of the display device 208 that corresponds to the imaging mode in which the ultrasound image 302 is to be obtained. The controller 210 then switches the imaging mode of the system 200.

One or more of the user selectable elements 322 through 330 (in one embodiment, the "Soft key" areas 322 through 330) represents a control, operation, function, image adjustment, and the like, associated with an input component of the input device 214. For example, each of the "Soft key" areas 322 through 330 may represent a keystroke, key or button on a keyboard of the input device 214. Touching a "Soft key" area 322 through 330 causes the system 200 to perform the same control, operation, function, image adjustment, and the like, that normally is associated with the associated keystroke, key or button on the input device 214 in one embodiment. In one embodiment, the controls, operations, functions, adjustments, and the like, associated with the "Soft key" areas 322 through 330 change based on the imaging mode currently employed by the system 200. For example, the "Soft key" areas 322 through 330 may be associated with a group of image adjustments when the system 200 is acquiring the ultrasound image 302 in B-mode imaging. The "Soft key" areas 322 through 330 may be associated with a different group of image adjustments when the system 200 is acquiring the ultrasound image 302 in PDI mode imaging.

For example, when the system 200 is acquiring the ultrasound image 302 using B-mode imaging, the "Soft key" areas 322 through 330 may be associated with one group of imaging controls. The "Soft key" area 322 may be associated with activating and deactivating a spatial compounding technique used in acquiring and generating the ultrasound image 302. In one embodiment, touching the "Soft key" area 322 activates or deactivates a CrossXbeam™ spatial compounding technique provided by GE Healthcare.

The "Soft key" area 324 may be associated with activating and deactivating a harmonic imaging technique used by the system 200 to acquire and display the ultrasound image 302. The harmonic imaging technique includes filtering out the ultrasound beams emitted by the transducer elements 104 (shown in FIG. 1) and viewing the image generated from the higher frequency signals generated by tissue. For example, when an ultrasound beam passes through human tissue, the ultrasound beam can generate signals at higher frequencies due to non-linear propagation of the ultrasound beams emitted by the transducer elements 104. These higher frequencies also are referred to as harmonics. The system 200 may generate the ultrasound image 302 based on these higher frequency signals.

The "Soft key" area 326 may be touched to enhance a presentation or visualization of an associated peripheral device or apparatus in the ultrasound image 302. For example, touching the "Soft key" area 326 may cause the display device 208 to change one or more of a color, contrast, sharpness, and the like, of an image of a needle inside the body part being imaged in the ultrasound image 302. GE Healthcare's B-Steer Plus technology is one example of such a function that can be activated and deactivated using the "Soft key" area 326.

The "Soft key" area 328 may be touched to activate and deactivate the display of a virtual apex of a sector transducer probe and/or a virtual convex of a linear transducer probe on the ultrasound image 302. For example, where the transducer 204 (shown in FIG. 2) used to obtain the ultrasound image 302 is a sector probe, the virtual apex of the transducer 204 may be shown on the ultrasound image 302 by the display device 208 when the "Soft key" area 328 is touched and the virtual apex may cease to be displayed when the "Soft key" area 328 is touched a second time. In another example, where the transducer 204 used to obtain the ultrasound image 302 is a linear probe, the virtual convex of the transducer 204 may be shown on the ultrasound image 302 by the display device 208 when the "Soft key" area 328 is touched and the virtual convex may cease to be displayed when the "Soft key" area 328 is touched a second time.

The "Soft key" area 330 may be touched to activate and deactivate the display of vascular bodies in the imaged body shown in the ultrasound image 302. For example, touching the "Soft key" area 330 may cause the flow of blood through the imaged body to be shown in the ultrasound image 302. Touching the "Soft key" area 330 a second time may cause the flow of blood through the imaged body to no longer be shown in the ultrasound image 302.

In another example, the "Soft key" areas 322 through 330 may be associated with a different group of imaging controls when the system 200 is acquiring the ultrasound image 302 using color mode imaging or PDI mode imaging. The "Soft key" area 322 may be associated with changing the size of the imaged area in the body being displayed in the ultrasound image 302. For example, the system 200 initially may display a portion of the ultrasound image 302 in color while the remainder of the ultrasound image 302 is displayed in black and white on the display device 208. In one embodiment, a box (not shown) that is approximately 30% of the total size of the ultrasound image 302 initially is shown on the display device 208 with the portion of the ultrasound image 302 in the box being in color. Touching the "Soft key" area 322 may incrementally increase or decrease the size of the box, or the portion of the ultrasound image 302 that is shown in color. Alternatively, touching the "Soft key" area 322 may graphically populate a numerical keypad, sliding bar, or other graphical input object, that can be manipulated by touching the display device 208 to increase and/or decrease the size of the portion being displayed in color. In another embodiment, the operator can select and drag one or more corners of the ultrasound image 302 to change the size of the image.

The "Soft key" area 324 may be associated with changing the direction that the ultrasound beams emitted from the transducer elements 104 (shown in FIG. 1) are emitted. For example, touching the "Soft key" area 324 may toggle a steering direction of the ultrasound beams. The ultrasound beams initially are emitted toward a center of the imaged body, and touching the "Soft key" area 324 can change the steering direction between left, center and right, which adjustment may be incrementally performed.

In another example, the "Soft key" area 332 may be associated with a different imaging function when the system 200 is acquiring the ultrasound image 302 using M-mode imaging. The "Soft key" area 322 may be associated with a function that automatically measures a size of a feature shown in the imaged body on the ultrasound image 302. For example, touching the "Soft key" area 322 can direct the system 200 to automatically determine a linear distance between two points on an ultrasound waveform that is received by the transducer elements 104 (shown in FIG. 1).

In another example, the "Soft key" areas 332 through 328 may be associated with a different group of imaging functions or operations when the system 200 is acquiring the ultrasound image 302 using PW-mode imaging. The "Soft key" area 322 may be associated with a function that inverts the ultrasound image 302 each time the "Soft key" area 322 is touched. The "Soft key" area 324 may increase a baseline level each time the "Soft key" area 324 is touched, while the "Soft key" area 326 may decrease the baseline level each time the "Soft key" area 326 is touched. In one embodiment, the baseline level is the minimum signal level of received ultrasound beams that is displayed on the ultrasound image 302. Increasing the baseline level can cause weaker signals associated with some ultrasound beams to not be shown in the ultrasound image 302, while decreasing the baseline can cause more signals to be shown. The "Soft key" area 326 may change the viewing angle from which the ultrasound image 302 is acquired in the imaged body. For example, each time the "Soft key" area 326 is touched, the viewing angle of the ultrasound image 302 may increase or decrease.

In one embodiment, touching the user selectable element 320 on the display device 208 causes a different group or set of imaging functions to be associated with one or more of the "Soft key" areas 322 through 326. For example, the "Soft key" area 322 may be associated with a reverse loop function that plays a video of the plurality of the ultrasound images 302. The video includes a collection of ultrasound images 302 that are presented in an order in reverse of the order in which the images 302 were obtained. Touching the "Soft key" area 322 can cause the system 200 to play the video of the ultrasound images 302 in the reverse order. Conversely, touching the "Soft key" area 326 can cause the system 200 to play the same video in a forward direction, or to present the ultrasound images 302 in the video in the same order that the ultrasound images 302 were obtained. Touching the "Soft key" area 324 can pause the ultrasound image 302 so that the ultrasound image 302 becomes a static image. For example, the system 200 may acquire and present the ultrasound image 302 in real time such that movement of the patient and/or transducer 104 (shown in FIG. 1) causes the ultrasound image 302 to correspondingly move. Touching the "Soft key" area 324 can pause the display of the ultrasound image 302 shown on the display device 208 so that the ultrasound image 302 is a static image. Touching the "Soft key" area 324 a second time can return the system 200 to displaying the ultrasound image 302 as a real time, moving image.

In one embodiment, the text displayed on the "Soft key" areas 322 through 330 may change to correspond with the control, operation, function, image adjustment, and the like, currently associated with the "Soft key" areas 322 through 330. The text displayed on the "Soft key" areas 322 through 330 may change for other controls in different embodiments. The Figures only illustrate one example labeling scheme, and others are possible and within the scope of one or more embodiments described herein. For example, one or more of the "Soft key" areas 322 through 330 may be user programmable such that an operator can change the text displayed on one or more of the "Soft key" areas 322 through 330.

In the embodiment illustrated in FIG. 3, the ultrasound image 302 and the user selectable elements 310 through 340 are concurrently displayed on the display device 208. For example, the ultrasound image 302 and the user selectable elements 310 through 340 are presented on the display device 208 in separate, non-overlapping areas of the display device 208 such that the ultrasound image 302 is not significantly obscured by one or more of the user selectable elements 310 through 340. The user selectable elements 310 through 340 thus may be displayed and used to adjust the ultrasound image 302 at the same time that the ultrasound image 302 is displayed on the display device 208.

In one embodiment, the system 200 permits the operator to touch one or more of the user selectable elements 310 through 340 as the ultrasound image 302 is obtained and/or displayed on the display device 208. For example, one or more of the user selectable elements 310 through 340 may be employed to adjust one or more settings of the system 200 to adjust the acquisition with display of the ultrasound image 302.

The set of user selectable elements 310 through 340 that is displayed in one or more of the touch sensitive portions 304 through 308 is customizable in one embodiment. For example, an operator can select one or more of the user selectable elements 310 through 340 to be presented on the display device 208 in one or more of the touch sensitive portions 304 through 308. The operator can customize which user selectable elements 310 through 340 are presented and save which user selectable elements 310 through 340 for later retrieval. For example, the set of user selectable elements 310 through 340 that is selected by the operator can be saved in one or more of the computer-readable storage media 114, 120.

Figure 5:
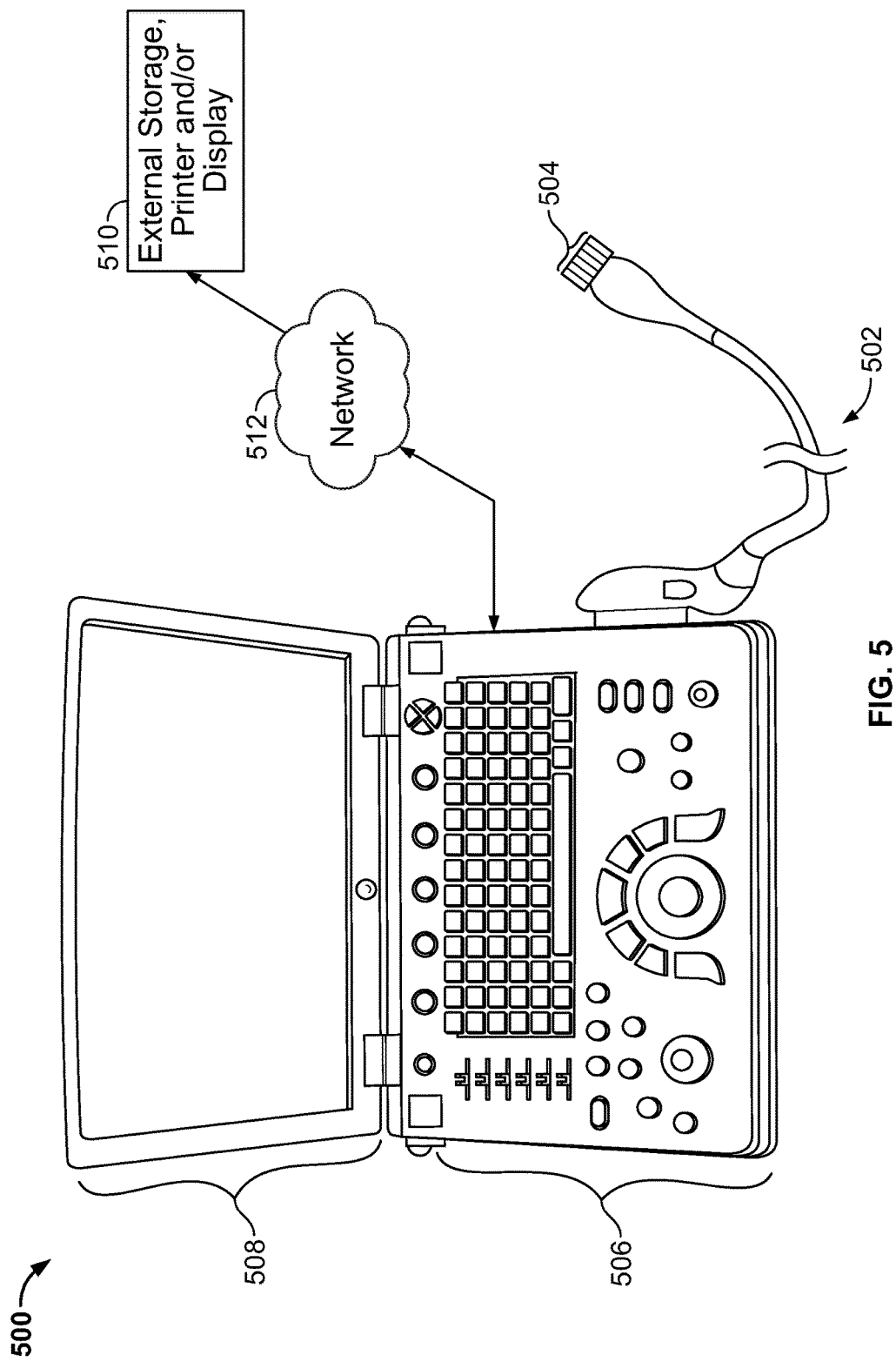
FIG. 5 illustrates a miniaturized ultrasound imaging system having a display device that may be configured to include one or more touch sensitive portions and user selectable elements similar to the display device shown in FIG. 2.

FIG. 5 illustrates a miniaturized ultrasound imaging system 500 having a display device 502 that may be configured to include one or more touch sensitive portions and user selectable elements similar to the display device 208 shown in FIG. 2. For example, a transducer 502 may have an array of transducer elements 504 similar to the transducer 106 and transducer elements 104 shown in FIG. 1. A user interface 506 is provided and is similar to the user interface 214 (shown in FIG. 2) in one embodiment. As used herein, "miniaturized" means that the ultrasound system 500 is a handheld or hand-carried device or is configured to be carried in a person's hand, pocket, briefcase-sized case, or backpack. For example, the ultrasound system 500 may be a hand-carried device having a size of a typical laptop computer, for instance, having dimensions of approximately 2.5 inches in depth, approximately 14 inches in width, and approximately 12 inches in height. The ultrasound system 500 may weigh about ten pounds, and thus is easily portable by the operator.

An integrated display device 508 (for example, an internal display) is also provided and is similar to the display device 208 (shown in FIG. 2). For example, the display device 508 includes one or more touch sensitive portions (not shown) similar to the touch sensitive portions 304 through 308 (shown in FIG. 3) and present one or more user selectable elements (not shown) similar to the user selectable elements 310 through 340 (shown in FIG. 3). The user selectable elements of the display device 508 are used to adjust an ultrasound image presented on the display device 508 and/or one or more imaging settings of the system 500. The display device 508 may concurrently present the ultrasound image and the user selectable elements, similar to as described above with respect to the display device 208.

Imaging data obtained with the transducer 502 may be sent to an external device 510 via a wired or wireless network 512 (or direct connection, for example, via a serial or parallel cable or USB port). In some embodiments, the external device 510 may be a computer or a workstation having a display. Alternatively, the external device 510 may be a separate external display or a printer capable of receiving image data from the system 500 and of displaying or printing images that may have greater resolution than the display device 508.

Figure 6:
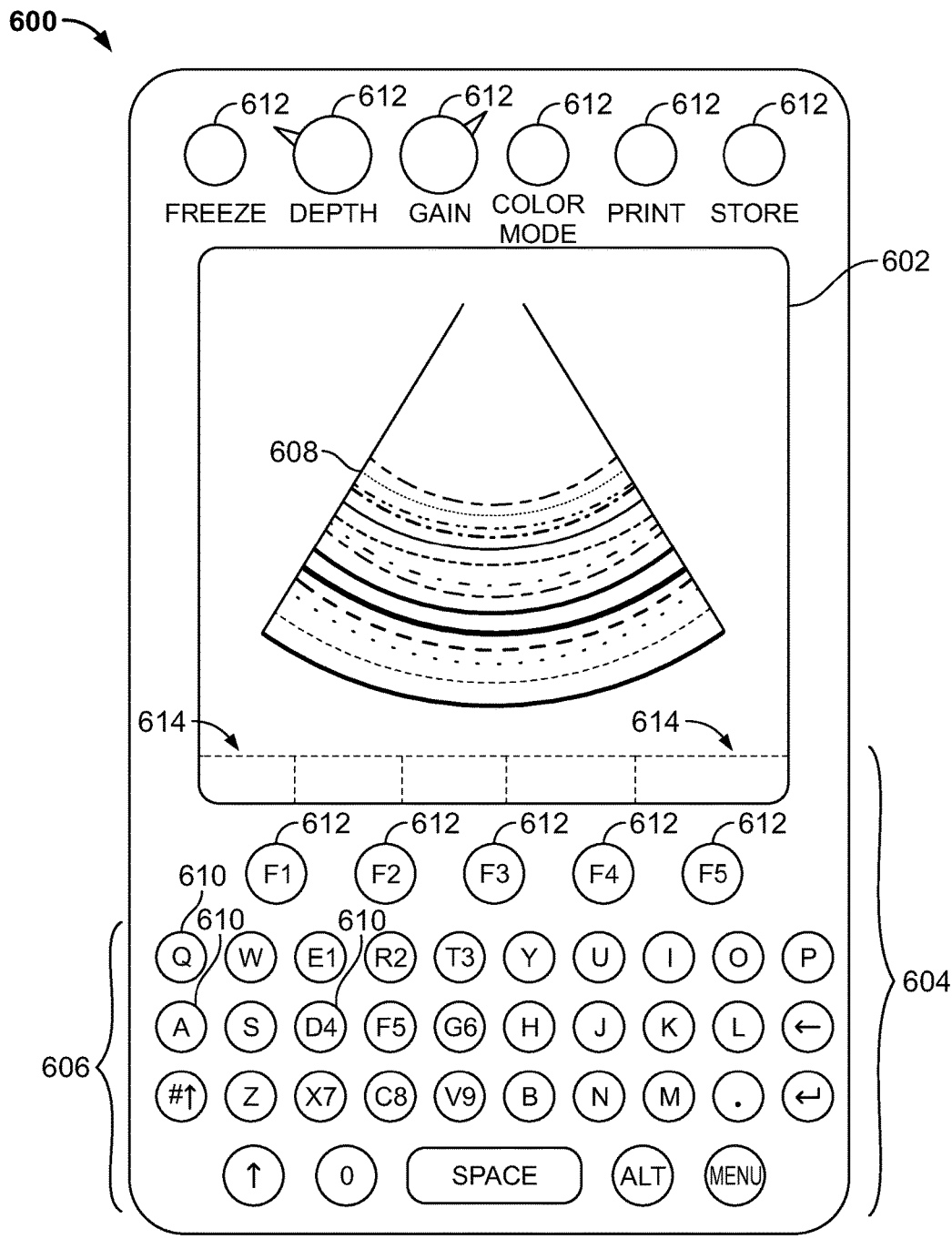
FIG. 6 illustrates a hand carried or pocket-sized ultrasound imaging system that may be configured to include one or more touch sensitive portions and user selectable elements similar to the display device shown in FIG. 2.

FIG. 6 illustrates a hand carried or pocket-sized ultrasound imaging system 600 that may be configured to include one or more touch sensitive portions and user selectable elements similar to the display device 208 shown in FIG. 2. The system 600 includes a display 602 that is similar to the display device 208. For example, the display 602 may include one or more touch sensitive portions 614 similar to the touch sensitive portions 304 through 308 (shown in FIG. 3) and present one or more user selectable elements (not shown) similar to the user selectable elements 310 through 340 (shown in FIG. 3). The user selectable elements of the display 602 are used to adjust an ultrasound image presented on the display 602 and/or one or more imaging settings of the system 600. The display 602 may concurrently present the ultrasound image and the user selectable elements, similar to as described above with respect to the display device 208. The system 600 includes a user interface 604 that is similar to the user interface 214 (shown in FIG. 2).

In the illustrated embodiment, the display 602 and user interface 604 form a single unit. By way of example, the system 600 may be a pocket-sized or hand-sized ultrasound system approximately 2 inches wide, approximately 4 inches in length, and approximately 0.5 inches in depth and weighs less than 3 ounces. The display 602 may be, for example, a 320×320 pixel touch sensitive color LCD display (on which an ultrasound image 608 similar to the ultrasound image 302 (shown in FIG. 3) may be displayed). A typewriter-like keyboard 606 of buttons 610 may optionally be included in the user interface 604. It should be noted that the various embodiments may be implemented in connection with a pocket-sized ultrasound system 600 having different dimensions, weights, and power consumption. Multi-function controls 612 may each be assigned functions in accordance with the mode of system operation. Therefore, each of the multi-function controls 612 may be configured to provide a plurality of different actions.

Figure 7:
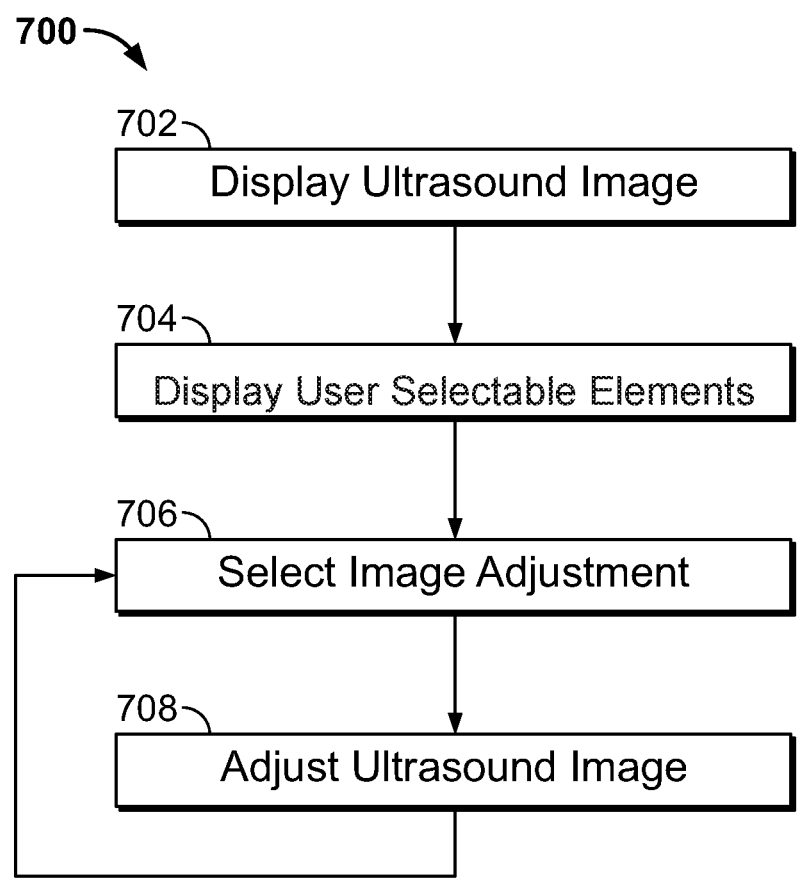
FIG. 7 is a flowchart of a method for presenting an ultrasound image according to one embodiment.

FIG. 7 is a flowchart of a method 700 for presenting an ultrasound image according to one embodiment. While the actions of the method 700 are illustrated as functional blocks, the order of the blocks and the separation of the actions among the various blocks shown in FIG. 7 is not intended to be limiting. For example, the blocks may be performed in a different order and an action associated with one block may be combined with one or more other blocks or may be subdivided into a plurality of blocks.

At 702, an ultrasound image is displayed. For example, the ultrasound image 302 (shown in FIG. 3) may be displayed on the display device 208 (shown in FIG. 2). At 704, one or more user selectable elements are displayed. For example, one or more of the user selectable elements 310 through 340 (shown in FIG. 3) may be displayed on one or more touch sensitive areas 304 through 308 (shown in FIG. 3) on the display device 208. In one embodiment, the ultrasound image and the user selectable element(s) are concurrently displayed, as described above.

At 706, one or more image adjustments are selected. For example, the user selectable elements displayed at 704 may be associated with a plurality of functions, operations, settings, controls, and the like, associated with operation of the ultrasound imaging system 200 (shown in FIG. 2). Touching one or more of the user selectable elements on the display device 208 selects a corresponding function, operation, control, and the like, and allows altering or adjusting one or more of these functions, operations, settings, controls, and the like.

At 708, the ultrasound image is adjusted based on the image adjustment(s) selected at 706. For example, selecting a graphically displayed area at 706 can increase a gain of the system 200. As a result, the presentation of the ultrasound image may be adjusted or altered based on the increased gain of the system 200. In one embodiment, the method 700 proceeds between 708 and 706 in a loop-wise manner. For example, additional image adjustments can be selected and applied to adjust the display of the ultrasound image. Alternatively, the method 700 may terminate after 708.

Figure 8:
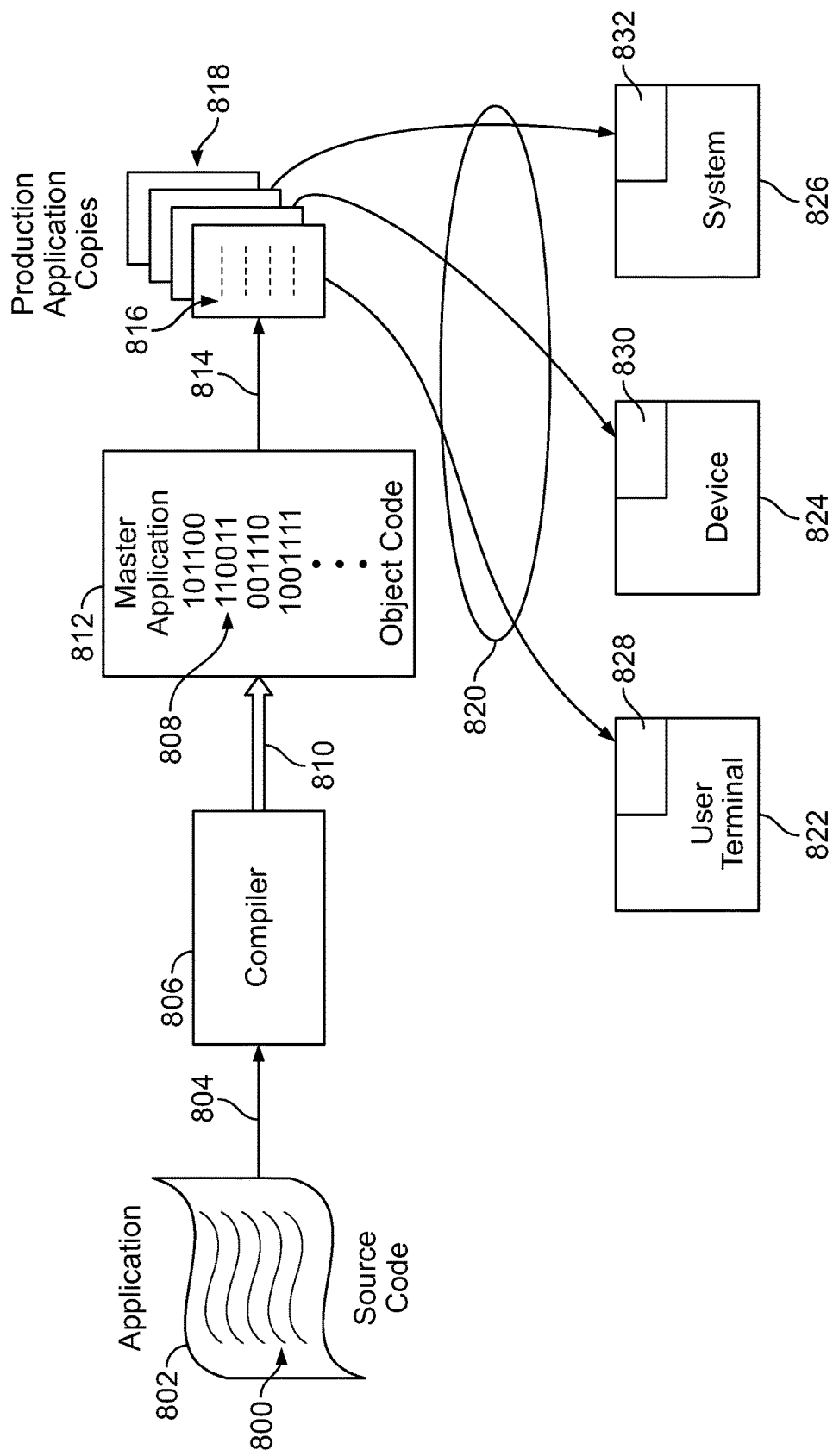
FIG. 8 illustrates a block diagram of exemplary manners in which embodiments of the present invention may be stored, distributed and installed on a computer-readable medium.

FIG. 8 illustrates a block diagram of exemplary manners in which embodiments of the present invention may be stored, distributed and installed on a computer-readable medium. In FIG. 8, the "application" represents one or more of the methods and process operations discussed above. For example, the application may represent the process carried out in connection with FIGS. 1 through 7 as discussed above.

As shown in FIG. 8, the application is initially generated and stored as source code 800 on a source computer-readable medium 802. The source code 800 is then conveyed over path 804 and processed by a compiler 806 to produce object code 808. The object code 808 is conveyed over path 810 and saved as one or more application masters on a master computer-readable medium 812. The object code 808 is then copied numerous times, as denoted by path 814, to produce production application copies 816 that are saved on separate production computer-readable medium 818. The production computer-readable medium 818 is then conveyed, as denoted by path 820, to various systems, devices, terminals and the like. In the example of FIG. 8, a user terminal 822, a device 824 and a system 826 are shown as examples of hardware components, on which the production computer-readable medium 818 are installed as applications (as denoted by 828 through 832). For example, the production computer-readable medium 818 may be installed on the controller 210 shown in FIG. 2.

The source code may be written as scripts, or in any high-level or low-level language. Examples of the source, master, and production computer-readable medium 802, 812 and 818 include, but are not limited to, CDROM, RAM, ROM, Flash memory, RAID drives, memory on a computer system and the like. Examples of the paths 804, 810, 814, and 820 include, but are not limited to, network paths, the internet, Bluetooth, GSM, infrared wireless LANs, HIPER-LAN, 3G, satellite, and the like. The paths 804, 810, 814, and 820 may also represent public or private carrier services that transport one or more physical copies of the source, master, or production computer-readable medium 802, 812 or 818 between two geographic locations. The paths 804, 810, 814 and 820 may represent threads carried out by one or more processors in parallel. For example, one computer may hold the source code 800, compiler 806 and object code 808. Multiple computers may operate in parallel to produce the production application copies 816. The paths 804, 810, 814, and 820 may be intra-state, inter-state, intra-country, inter-country, intra-continental, inter-continental and the like.

The operations noted in FIG. 8 may be performed in a widely distributed manner world-wide with only a portion thereof being performed in the United States. For example, the application source code 800 may be written in the United States and saved on a source computer-readable medium 802 in the United States, but transported to another country (corresponding to path 804) before compiling, copying and installation. Alternatively, the application source code 800 may be written in or outside of the United States, compiled at a compiler 806 located in the United States and saved on a master computer-readable medium 812 in the United States, but the object code 809 transported to another country (corresponding to path 814) before copying and installation. Alternatively, the application source code 800 and object code 808 may be produced in or outside of the United States, but production application copies 816 produced in or conveyed to the United States (for example, as part of a staging operation) before the production application copies 816 are installed on user terminals 822, devices 824, and/or systems 826 located in or outside the United States as applications 828 through 832.

As used throughout the specification and claims, the phrases "computer-readable medium" and "instructions configured to" shall refer to any one or all of (i) the source computer-readable medium 802 and source code 800, (ii) the master computer-readable medium and object code 808, (iii) the production computer-readable medium 818 and production application copies 816 and/or (iv) the applications 828 through 832 saved in memory in the terminal 822, device 824 and system 826.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for displaying ultrasound images, the system comprising:
   a base including a controller for controlling an ultrasound transducer to acquire an ultrasound image, wherein the controller includes one or more processors and is configured to generate the acquired ultrasound image; and
   first and second display devices coupled with the base, the first display device being a primary display including a monitor and the second display device being a touch screen display, wherein the first and second displays are each directed by the controller to display the acquired ultrasound image and the second display device is further configured for a user to perform one or more measurements on the displayed ultrasound image, the first display device includes a plurality of user selectable elements, wherein only a subset of the user selectable elements from the first display device is replicated on the second display device, the subset of user selectable elements includes at least one of a new patient area, a comment area, a measure area, a depth adjustment area, a gain adjustment area, a focal position adjustment area, an auto optimize area, or a soft key area, wherein the controller is configured to process one or more user inputs relating to the measurements.

2. The system of claim 1, wherein at least one of the user selectable elements of the plurality of user selectable elements of the second display device correspond to image adjustments, the controller adjusting the ultrasound image according to one of the image adjustments when the at least one of the user selectable elements displayed on the touch screen display is touched.

3. The system of claim 1, wherein the first display device includes an input device having at least one physical user input device, wherein the at least one physical user input device corresponds to at least one of the plurality of user selectable elements of the first display device.

4. The system of claim 3, wherein one of the user selectable elements corresponds to a graphical control indicator displayed on the first display device or the second display device, the graphical control indicator indicating when selections on the second display device or the input device controls the system.

5. The system of claim 1, further comprising a user interface communicatively coupled to the controller, the user interface having at least one physical user input device, the controller configured to adjust the ultrasound image based on input from the user interface, wherein the controller is responsive to one of the user interface or the second display device at a given time to adjust the ultrasound image.

6. The system of claim 1, wherein the plurality of user selectable elements of the second display device change based on a current imaging mode of the system.

7. The system of claim 1, wherein the plurality of user selectable elements of the second display device correspond to touch sensitive portions of the touch screen display and are responsive to touch to permit an operator to select one of the plurality of user selectable elements corresponding to a function or operation of the system.

8. The system of claim 1, wherein at least one of the first or second display devices comprises a color touch screen.

9. The system of claim 1, wherein the second display device is programmable to customize one or more of the plurality of user selectable elements presented on the second display device based on a user's preference.

10. The system of claim 1, further comprising a bracket interconnecting the first and second display devices.

11. The system of claim 1, wherein one of the first or second display devices is disposed above the other one of the first or second display devices.

12. The system of claim 1, further comprising a USB port configured to communicate image data to an external device.

13. The system of claim 1, further comprising a dedicated button programmed to select an image adjustment when depressed by an operator.

14. The system of claim 1, wherein at least one of the first or second display devices is configured to be folded downward toward a separate input device.

15. The system of claim 1, wherein the plurality of user selectable elements of the first and second display devices correspond to one or more measurement functions.

16. The system of claim 1, wherein a first group of the plurality of user selectable elements presented on the second display device is associated with a first group of image adjustments or imaging controls for a first imaging mode and a second group of the plurality of user selectable elements presented on the second display device is associated with a second group of image adjustments or imaging controls for a second imaging mode different than the first imaging mode.

17. The system of claim 1, wherein a subset of the plurality of user selectable elements presented on the second display device is associated with a current scanning session.

18. The system of claim 1, wherein the first and second display devices are configured to permit the operator to select the user selectable elements on both the first display device and the second display device in a first mode of operation and to select the same user selectable elements on one of the first display device or the second display device in a second mode of operation while both the first and second display devices remain coupled to the base.

19. The system of claim 1, wherein the base is a movable base comprising a plurality of wheels and configured to support thereon the ultrasound transducer.

20. The system of claim 1, wherein the second display is configured to permit a user to perform measurements on the displayed image by prompting the user to identify two or more points on the displayed image between or among which a measurement is to be made.

21. The system of claim 1, wherein the acquired ultrasound image is displayed concurrently on the first and second display devices.

22. The system of claim 1, further comprises a computer readable memory, wherein the computer readable memory is configured to save the displayed ultrasound image along with the one or more measurements.

23. A method for presenting an ultrasound image obtained by an ultrasound system, the method comprising:
displaying, while a first display device and a second display device remain coupled to a common base, an ultrasound image on the first display device being a primary display including a monitor, and displaying the ultrasound image on the second display device being a touch screen display, the ultrasound image acquired by an ultrasound transducer controlled by a controller in the common base, wherein the first display device includes a plurality of user selectable elements, wherein only a subset of the user selectable elements from the first display device is replicated on the second display device, the subset of user selectable elements includes at least one of a new patient area, a comment area, a measure area, a depth adjustment area, a gain adjustment area, a focal position adjustment area, an auto optimize area, or a soft key area, the plurality of user selectable elements of the second display device correspond to a touch sensitive portion of the touch screen display that encompasses the plurality of user selectable elements;
receiving a user input at the touch screen display to perform one or more measurements on the displayed image; and
processing the user input to perform the one or more measurements.

24. The method of claim 23, further comprising displaying the ultrasound image and the plurality of user selectable elements in separate, non-overlapping areas of one or more of the first and second display devices.

25. The method of claim 23, further comprising customizing which of the subset of the user selectable elements is presented on the second display device.

26. The method of claim 23, further comprising concurrently displaying the plurality of user selectable elements within touch sensitive portions of both the first and second display devices in a first mode of operation and displaying the plurality of user selectable elements within the touch sensitive portion of one of the first or second display devices in a second mode of operation while the first and second display devices remain coupled to a common base.

27. A non-transitory computer-readable storage medium for adjusting a display of an ultrasound image obtained using an ultrasound system, the medium comprising:
   instructions for displaying the ultrasound image on a first display device being a primary display and a second display device being a touch screen display, the first display device include a plurality of user selectable elements, wherein only a subset of user selectable elements from the first display device is replicated on the second display device, the subset of user selectable elements includes at least one of a new patient area, a comment area, a measure area, a depth adjustment area, a gain adjustment area, a focal position adjustment area, an auto optimize area, or a soft key area, the plurality of user selectable elements of the second display device are within one or more touch sensitive portions of the touch screen display and being reconfigurable;
   instructions for sensing touch of the touch screen display to perform one or more measurements on the displayed image while the first and second display devices remain coupled to a common base; and
   instructions for processing an input corresponding to the touch to perform the one or more measurements.

28. The computer-readable storage medium of claim 27, further comprising instructions for switching control the user interface having at least one physical user input device.

29. The computer-readable storage medium of claim 27, wherein the instructions for displaying comprise instructions for customizing which of the plurality of user selectable elements is displayed based on a user's preference.

30. The computer-readable storage medium of claim 27, wherein the instructions for displaying comprise instructions for customizing which of the plurality of user selectable elements is displayed based on a current imaging mode of the ultrasound system.

31. The computer-readable storage medium of claim 27, wherein the first and second display devices are configured to switch from a first mode of operation to a second mode of operation when the at least one of the first or second display devices is folded downward and further comprising instructions for sensing touch of one of the plurality of the user selectable elements to select a corresponding image adjustment or imaging setting on both the first and second display devices in the first mode of operation and instructions for sensing touch of one of the plurality of the user selectable elements on one of the first or second display devices in the second mode of operation.

32. The computer-readable storage medium of claim 31, further comprising instructions for concurrently displaying the ultrasound image on the first display device and the second display device.

* * * * *